(12) United States Patent
Trakumas et al.

(10) Patent No.: US 7,073,402 B2
(45) Date of Patent: Jul. 11, 2006

(54) AIR SAMPLER WITH PARALLEL IMPACTORS

(75) Inventors: Saulius Trakumas, Pittsburgh, PA (US); Peter M. Hall, Venetia, PA (US)

(73) Assignee: SKC, Inc., Eighty Four, PA (US)

( * ) Notice: Subject to any disclaimer, the term of this patent is extended or adjusted under 35 U.S.C. 154(b) by 358 days.

(21) Appl. No.: 10/639,564

(22) Filed: Aug. 12, 2003

(65) Prior Publication Data

US 2005/0279181 A1   Dec. 22, 2005

(51) Int. Cl.
*G01N 1/24* (2006.01)
*G01N 1/40* (2006.01)

(52) U.S. Cl. ............... 73/863.22; 73/863.31
(58) Field of Classification Search ...............
      73/863.21–863.31; 703/1
See application file for complete search history.

(56) References Cited

U.S. PATENT DOCUMENTS

| | | | |
|---|---|---|---|
| 2,675,697 A * | 4/1954 | Quynn et al. ............ 73/863.22 |
| 3,633,405 A * | 1/1972 | Noll ............................. 73/28.06 |
| 3,741,001 A * | 6/1973 | Fletcher et al. ............ 73/28.05 |
| 3,983,743 A | 10/1976 | Olin et al. |
| 4,038,057 A | 7/1977 | Roth |
| 4,133,202 A | 1/1979 | Marple |
| 4,159,635 A | 7/1979 | Sehmel |
| 4,391,151 A | 7/1983 | Nelson et al. |
| 4,570,494 A | 2/1986 | Dunn et al. |
| 4,670,135 A * | 6/1987 | Marple et al. .............. 209/143 |
| 4,764,186 A * | 8/1988 | Langer ........................ 95/268 |
| 4,926,679 A | 5/1990 | Dewhurst |
| 4,972,957 A | 11/1990 | Liu et al. |
| 5,128,539 A * | 7/1992 | Rodgers et al. ............ 250/255 |
| 5,317,930 A | 6/1994 | Wedding |
| 5,412,975 A | 5/1995 | Raabe et al. |
| 5,437,198 A | 8/1995 | John |
| 5,932,795 A | 8/1999 | Koutrakis et al. |
| 6,122,054 A | 9/2000 | Ence |
| 6,216,548 B1 * | 4/2001 | Park et al. ............... 73/863.02 |
| 6,349,668 B1 | 2/2002 | Sun et al. |
| 6,435,043 B1 | 8/2002 | Ferguson et al. |
| 6,553,848 B1 | 4/2003 | Tallentire et al. |
| 6,695,146 B1 * | 2/2004 | Call et al. ............. 73/863.22 X |

FOREIGN PATENT DOCUMENTS

EP            61074 A  *  9/1982

OTHER PUBLICATIONS

International Organization For Standardization (ISO), "Air Quality - particle Size Fraction Definitions for Health-Related Sampling—ISO 7708," International Standard, International Organization for. Apr. 1995, pp. 6-20 & pp. 1-9.

(Continued)

*Primary Examiner*—Thomas P. Noland
(74) *Attorney, Agent, or Firm*—William L. Krayer (57) ABSTRACT

An air sampler is designed for a predetermined flow rate. The air flow is admitted to at least two impactors operating in parallel. Preferably the inlet nozzles and the outlet orifices of each impactor are sized to achieve predetermined cut-off sizes of particles; preferably the composite curve of all the impactors will mimic a predetermined particle sampling efficiency curve.

7 Claims, 6 Drawing Sheets

OTHER PUBLICATIONS

Daniel J. Rader and Virgil A. Marple, "Effect of Ultra-Stokesian Drag and Particle Interception on Impaction Characteristics," Aerosol Science and Technology, p. 141-156, (No. 4, 1985). month not given.

Cheng-Hsiung Huang and Chuen-Jinn Tsai, "Influence of Impaction Plate Diameter and Particle Density on the Collection Efficiency of Round-Nozzle Inertial Impactors," Aerosol Science and Technology, Taylor and Francis, p. 714-720. (2002). No.36 month not given.

Cheng-Hsiung Huang, Chuen-Jinn Tsai, and Tung-Sheng Shih, "Particle Collection Efficiency of an Inertial Impactor with Porous Metal Substrates," Journal of Aerosol Science, Elsevier Science Ltd. p. 1035-1044, (2001). , No. 32, month not given.

Virgil A. Marple and Klaus Willeke, "Impactor Design," Atmospheric Environment, Pergamon Press (Great Britain), p. 891-896, (1976). vol. 15; month not given.

S. Trakumas and P. Hall, "Modification and Validation of Diesel Particulate Matter Cassette for PM1.0 Sampling at Different Flow Rates," Abstracts, American Industrial Hygiene Conference & Expo (San Diego CA, USA). p. 19-20. (Jun. 1-6, 2002).

Benjamin Jurcik and Hwa-Chi Wang, "On the Shape of Impactor Efficiency. Curves," Journal of Aerosol Science, Pergamon Press (Great Britain), vol. 26 (No. 7), p. 1139-1147, (1995). vol. 26, No. 7 month not given.

American Conference of Governmental Industrial Hygienists, "2003 TLVs and BEIs & Biological Exposure Indices," ACGIH (Cincinnati OH, USA), p. 74-77, (2003). month not given.

* cited by examiner

Air out
to Filter

Fig.3

Figure 5. Sampling efficiency measured for each individual impactor separately at sampling flow rate $Q_S=1.0$ L/min. These four impactors are designed to be incorporated into sampler approximating respirable curve at overall flow rate of 4.0 L/min.

Figure 6. Overall performance of four-impactor sampler at sampling flow rate $Q_S$=4.0 L/min.

Fig. 7

AIR SAMPLER WITH PARALLEL IMPACTORS

TECHNICAL FIELD

An air sampler divides incoming air into a plurality of parallel flows to separate collectors or collection chambers (sometimes known as impactors). A portion of the particles striking the separate impactors is retained and a portion of the particles in the sampled air continues through outlet orifices in the impactors for optional retention on a filter or other repository. While equal pressure drops are maintained across all collectors, the nozzles or orifices leading to each of the impactors have different effective areas in order to provide predetermined size-selective collection efficiencies at a selected overall air flow rate.

BACKGROUND OF THE INVENTION

Personal air samplers are designed to be worn by industrial workers and others who have reason for concern about particles, aerosols, microorganisms, fibers, and other small materials in the atmosphere they breathe. Since the air samplers are normally worn on the clothing of the user, they should be light in weight and unperturbed by more or less continual shifting of orientation, or even jostling. Generally, passive samplers—that is, those that are designed simply to detect the presence of a contaminant rather than to calculate a concentration—are quite light. The more elaborate samplers, designed to estimate or calculate a concentration of the collected material, must include a pump and an accurate way of determining the total flow of air through the sampler over a known period of time. Samplers including a pump and a battery for it tend to be heavier and more complicated than a passive sampler. It is generally desirable to simplify such samplers not only for the sake of expedient data collection, but also for convenience to the user.

Air samplers may be designed to collect specific types of contaminants or particulates, or for specific types of data collection. In particular, they may be designed to mimic penetration curves correlating the penetration into the lungs of particles and other materials of various sizes. The present invention is especially useful for size-selective sampling of industrial aerosols according to the definitions of inhalable, thoracic and respirable aerosols promulgated by ACGIH, the American Conference of Governmental Hygienists [2003 TLVs® and BEIs®: Threshold Limit Values for Chemical Substances and Physical Agents & Biological Exposure Indices, ACIGH, Cincinnati Ohio] and ISO, the International Organization for Standardization [International Standard: Air Quality-Particle Size Fraction Definitions for Health-Related Sampling. ISO 7708: 1995(E)—ISO, Geneva, Switzerland, 1995]. There is a need for a high-performance sampler which will remove the larger aerosols from the sampled air while permitting the remaining small ones, i.e. the respirable or thoracic portion, to pass through for subsequent collection or analysis.

A sampler having an entry plate with a tapered slit, leading to an impactor surface having a passage for particles not retained on the impactor surface is described by John in U.S. Pat. No. 5,437,198. The slit, the contour or the intake surface, and the impactor passage are designed so that the penetration efficiency at a known flow rate will follow a desired curve, i.e. a penetration efficiency vs. particle diameter plot is seen to mimic a prescribed curve. A downstream collector is designed to retain the particles passing through the impactor passage.

In U.S. Pat. No. 5,412,975, Rabbe et al direct particles larger than a cut size into a plurality of stagnation chambers. The stagnation chambers do not include exit ports, and the cut-off size is the same for all chambers.

Samplers having a series of cuts or consecutive stages, or cascading collecting devices in series, are shown by Dunn et al in U.S. Pat. No. 4,570,494, Olin et al in U.S. Pat. No. 3,983,743, and Liu et al U.S. Pat. No. 4,972,957.

A multiple nozzle, single stage impactor is disclosed by Marple in U.S. Pat. No. 4,133,202.

Equal flows of sampled air, provided by separate pumps, are illustrated in FIG. 5 of Koutrakis et al U.S. Pat. No. 5,932,795.

We are not aware of an air sampler in the prior art which splits an incoming air stream into two or more parallel paths for collection of particles in separate impactors according to different size-selection cut-offs, nor does it appear that such a device has been followed by combining the flow paths for collecting the remaining particles in a common repository.

SUMMARY OF THE INVENTION

The present invention divides an air sample stream into a plurality of flow streams, each of which is directed to a separate collector surface for collection of aerosols and particulates within a specified size range. The specified size range may be any range normally desired in an air sampler. The arrangement recognizes that the pressure drops across each of two or more impactors (collectors) in parallel in the same stream of air having a common inlet and a common outlet will be equal to the pressure drop across the entire sampler. While the sampler may be designed to provide equal flow rates in the parallel collectors, the flow rates need not be equal although the pressure drops will continue to be equal. A preferred way to assure a substantially constant flow rate is to draw the air through the sampler with a pump containing a built-in flow control system, such as the "AirChek2000"™ made by SKC, Inc. of Eighty Four, Pa. That is, exit orifices of all the parallel impactors or collectors will lead to a common chamber or tube which is connected to a pump capable of moving air at a constant flow rate through the sampler.

In a preferred configuration, the air sample stream is divided by directing the incoming air to a manifold or inlet plate having a plurality of sized orifices, hereafter sometimes called nozzles, each leading to a chamber having an impactor surface including a sized outlet orifice. The sizes of the nozzles are selected to achieve desired cuts in the particle sizes, taking into account also the shape of the desired curve the sampler is designed to follow, the overall sampling flow, and the number of collectors incorporated into the sampler. The outlet orifice in each collector is complementary to its inlet nozzle, in that it is selected in such a way as to assure that the flow rate in its collector will achieve a desired cut-off size selection. Air passing through the exit orifices enters a common passage and the remaining particles are collected, preferably on a filter.

The idea is based on the assumption that pressure drop across the impactor, ΔP, is approximately equal to the dynamic pressure in the nozzles:

$$\Delta P = \frac{1}{2}\rho V_0, \qquad (1)$$

where ρ is air density and $V_0$ is the average air velocity in the nozzle. Pressure drop across an individual collection chamber (impactor) or, $\Delta P_i$, is:

$$\Delta P_i = \Delta P_{iIn} + \Delta P_{iOut} \qquad (2)$$

Since all inlets of the collection chambers are at the same atmospheric pressure environment and all outlets connected to the single pump, the pressure drop across each individual collection chamber $\Delta P_i$ is the same and equal to the overall pressure drop across the whole sampler, $\Delta P_S$:

$$\Delta P_S = \Delta P_1 = \Delta P_2 = \ldots = \Delta P_N, \qquad (3)$$

Where N is the number of collectors in the sampler. Using equations 1, 2, and 3 we can write:

$$\frac{1}{2}\rho V_{1In}^2 + \frac{1}{2}\rho V_{1Out}^2 = \frac{1}{2}\rho V_{2In}^2 + \frac{1}{2}\rho V_{2Out}^2 = \ldots = \frac{1}{2}\rho V_{NIn}^2 + \frac{1}{2}\rho V_{NOut}^2, \qquad (4)$$

$$Q_1^2\left(\frac{1}{S_{1In}^2} + \frac{1}{S_{1Out}^2}\right) = Q_2^2\left(\frac{1}{S_{2In}^2} + \frac{1}{S_{2Out}^2}\right) = \ldots = Q_N^2\left(\frac{1}{S_{NIn}^2} + \frac{1}{S_{NOut}^2}\right), \qquad (5)$$

or where $Q_i$ is the flow rate through an individual collection chamber, and $S_{iIn}$ and $S_{iOut}$ are areas of inlet nozzles and outlet orifices of individual chambers.

The performance of an inertial impactor may be defined in terms of accomplishing 50% cut-off size, $d_{50}$—that is, 50% of particles this size penetrate through the impactor and another 50% are collected. $d_{50}$ can be found according to the equation:

$$d_{50} = \sqrt{\frac{9\mu W Stk_{50}}{\rho_p V_0 C}}, \qquad (6)$$

where μ is air viscosity, W is the width or diameter of the impactor nozzle, $Stk_{50}$ is the Stokes number corresponding to 50% particle cut-off, $\rho_p$ is the particle density, $V_0$ is average air velocity in the nozzle, and C is the size-dependent Cunningham slip correction factor. According to the impaction theory $Stk_{50}$ is also dependent on the Reynolds number of the flow through the nozzle, Re, jet-to-plate distance S, and impactor nozzle throat length T. Rader, D. J. and Marple, V. A., "Effect of Ultra-Stokesian Drag and Particle Interception on Impaction Characteristics," Aerosol Sci. Techno. 4:141–156 (1985); Marple, V. A. and Willeke, K., "Impactor Design," Atmos. Envir. 10:891–896 (1976).

The inlet nozzle area (i.e., diameter for a round nozzle or width and length of rectangular nozzle) for each individual collection chamber can be calculated for a selected $d_{50}$ and flow rate. Then the appropriate size of exit orifice can be found for each individual collection chamber using equation 5, still assuming equal flow rates are desired for all collectors. By selecting $d_{50}$ and flow rate for each individual collection chamber we may approximate any curve in a manner similar to that described by Marple in U.S. Pat. No. 4,133,202 (FIGS. 20 and 21). The Marple U.S. Pat. No. 4,133,202 is incorporated herein in its entirety.

In an ideal impactor (or collection surface in an impactor) all particles of a size smaller than $d_{50}$ would pass the impactor and all particles larger than $d_{50}$ should be collected. In reality, the collection efficiency curve is S-shaped. Although the actual collection efficiency of an impactor is hardly ever as sharp as predicted by theory it still is too steep for a conventional impactor to be used to sample respirable or thoracic dust, which are defined by gradually declining curves.

The collection efficiency curve of any shape may be approximated using two or more impactors in parallel with different cut-off characteristics. Marple's U.S. Pat. No. 4,133,202, which is incorporated herein by reference, describes a single stage impactor having a plurality of nozzles. That is, Marple introduces his air sample to parallel nozzles of sizes selected to achieve certain cut-offs, and the air is passed through the nozzles to a common impact surface. In our invention, sizes of inlet and outlet nozzles (orifices) are coordinated with the pressure drop across the entire impactor to provide the separate impactors with different particle cut-off characteristics in order to approximate predetermined collection efficiency curves. Such predetermined collection efficiency curves appear in the ACGIH and ISO publications mentioned above, and may sometimes be referred to as published sampling curve standards.

DETAILED DESCRIPTION OF THE INVENTION

The terms used in this description and in the claims are meant to have the usual meaning attributed to them by persons skilled in the art. But, in order to possibly minimize uncertainty, the following terms are further discussed in light of the context of their use in this application. Particle means any small particle, aerosol, microorganism, droplet of liquid substance, dust or the like which one may desire to collect in an air sampler. Collector or collection chamber can be used interchangeably to include any vessel used for the collection of particles. All of the collectors or collection chambers mentioned herein as a part of one of the variations of the invention will have at least one inlet nozzle and at least one way for the air to pass through it, as through one or more outlet orifices. An impactor is a collection chamber or collector; it usually has at least one particle-impervious surface, treated or not, having an enhanced ability to retain particles, but it may alternatively or additionally include a filter or other porous material for particle collection. Such surfaces, filters, and other materials may be called collector surfaces. A nozzle is a short conduit capable of passing air through it. It need not be circular or rectangular, as are some of the examples herein. As used herein, a nozzle is usually a hole through a plate, wall or manifold, and is used to conduct air flow. For convenience, we have generally referred to inlets to the impactors as nozzles or inlet nozzles, and outlets from the impactors or collectors as outlet orifices. An inlet plate is the term sometimes used herein to refer to the plate or other barrier which contains the nozzles. The inlet plate may be completely open to the atmosphere, where air is drawn into the sampler by a vacuum pump, or may form a wall of an inlet chamber for the incoming air sample, in which case it may optionally be referred to as a manifold. Parallel is used to describe impactors utilizing separate air flow paths through the sampler, in an analogy to usage as applied to electrical circuits, to distinguish from "series" or "in series." Some prior art air samplers use impactors in series, sometimes described as cascaded, i.e. where air flows through one impactor and exits into another impactor.

The invention described herein introduces a compact device containing two or more separate impactors (collectors) located in parallel. Each separate impactor has its own inlet nozzle, outlet or exit orifice, and collection substrate. Air streams exiting each separate impactor are combined to a single stream so that a single air moving device (pump) is used to operate the sampler.

Figure 1:
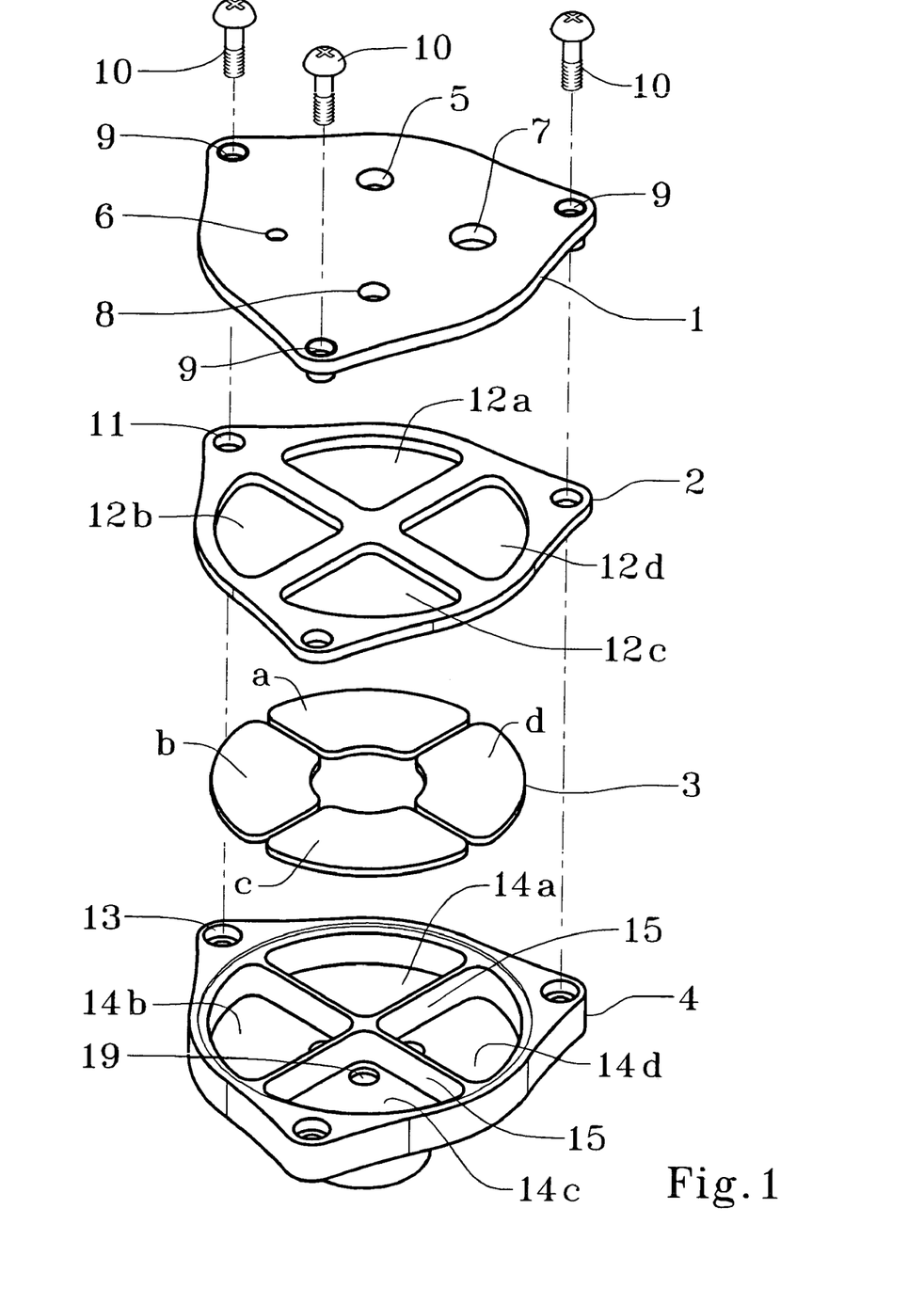
FIG. 1 is an exploded view of a preferred form of our parallel path sampler.

Referring now to FIG. 1, a preferred sampler of our design comprises inlet plate 1, gasket 2, impactor plate 3, and housing 4, held together by screws 10 in holes 9, 11, and 13. Inlet plate 1 has nozzles 5, 6, 7, and 8, each of a different diameter. Housing 4 has vertical dividers 15 which divide the space within housing 4 into four impact areas having a floor designated in four parts, 14*a*, 14*b*, 14*c*, and 14*d*. Gasket 2 seals the inlet plate 1 and housing 4, including the top edges of vertical dividers 15. Impactor plate 3 has four parts a, b, c, and d which are designed to rest on floor parts 14*a*, 14*b*, 14*c*, and 14*d*. The top surfaces of impactor plate parts a, b, c, and d may be made of or treated with a material selected to enhance its ability to retain particles. An outlet orifice 19 is visible; it should be noted that the outlet orifice 19 will not be covered by impactor plate part c, which occupies most of the area in floor part 14*c*. When fully assembled, the device will be seen to have formed four impactors, each having a single inlet nozzle 5, 6, 7, or 8, an impactor plate a, b, c, or d, and a single outlet orifice such as outlet orifice 19.

Figure 2:
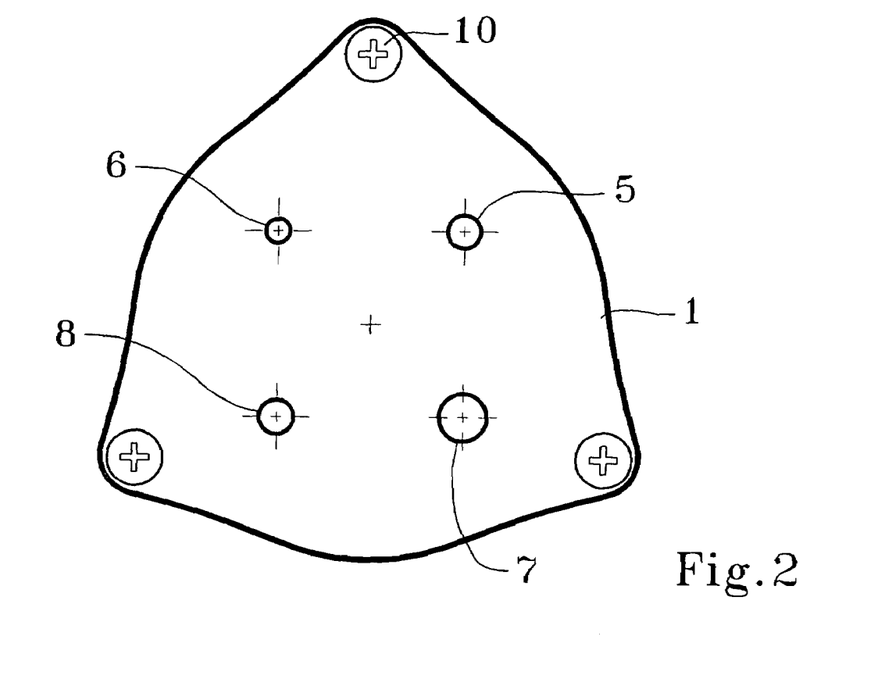
FIG. 2 is an exterior view of the inlet plate or manifold which covers the sampler of FIG. 1.

The different sizes of nozzles 5, 6, 7, and 8 are more clearly visible in FIG. 2.

Figure 3:
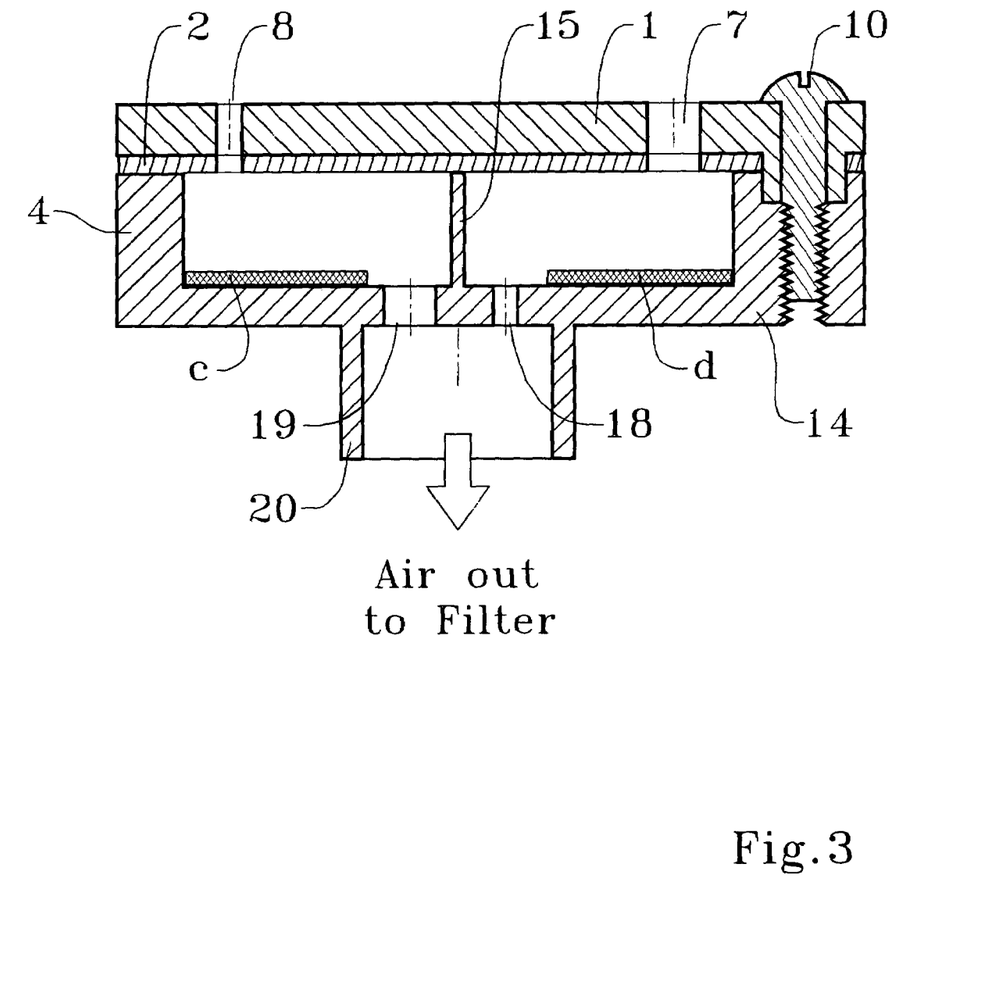
FIG. 3 is a section of the preferred sampler of FIG. 1.

In FIG. 3, the construction of the sampler is seen as a sectional view. Gasket 2 separates and seals inlet plate 1 and housing 4. Vertical divider 15 is seen to help define and separate the impactors on each side—that is, an impactor is defined on the left side, as depicted, by nozzle 8, impactor plate part c, and outlet orifice 19, and another impactor is defined on the right side, as depicted, by nozzle 7, impactor plate part d, and outlet orifice 18. Impactor plate parts c and d are shown resting on floor 14 of housing 4. Attached to housing 4 in this configuration is an exhaust 20 for outgoing air. Exhaust 20 will normally be connected to a vacuum pump, not shown, but a filter for collecting particles remaining in the exhaust air may be placed between exhaust 20 and the pump.

Figure 4:
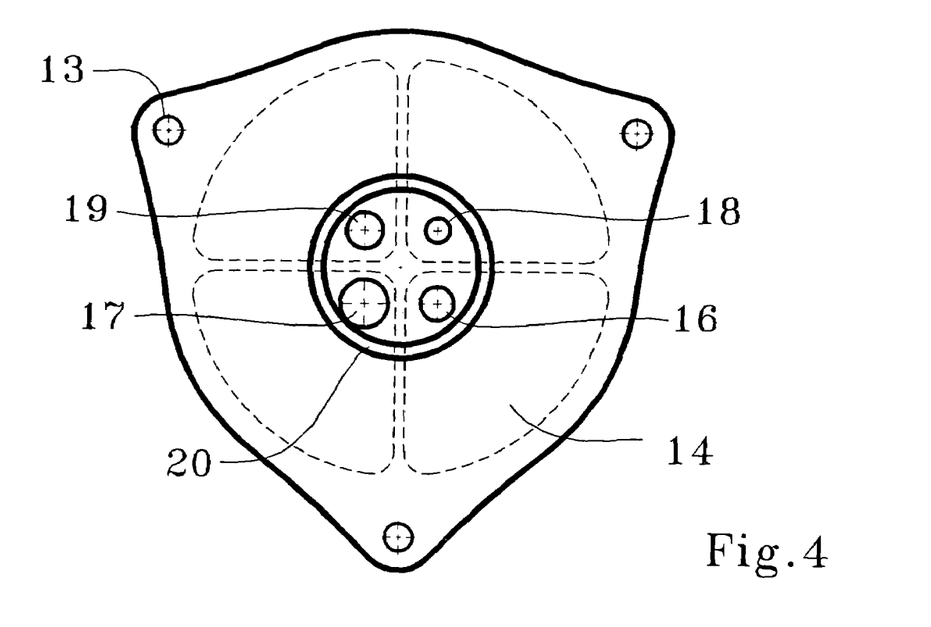
FIG. 4 is the bottom of the sampler of FIG. 1, showing the outlet orifices.

FIG. 4 is a view from the underside of the sampler, showing the exterior of floor 14, the exhaust 20, and outlet orifices 16, 17, 18, and 19, each serving a separate impactor. Holes 13 are for screws 10 to complete the assembly. Note again that outlet orifices 16, 17, 18, and 19 are of different sizes. As explained elsewhere herein, the sizes of the outlet orifices are selected to coordinate the flow rates of the individual impactors with the overall flow rate of the sampler, and to achieve desired predetermined size-selection cut-offs. Also it should be understood that, like the inlet nozzles, the outlet orifices need not be circular, rectangular or any other essential shape. Air proceeding out exhaust 20 comes from all four impactors and is mixed in exhaust 20. As indicated in the discussion of FIG. 3, the air may be sent to a filter capable, for example, of collecting other small particles which have not been collected in the impactors. But, exhaust 20 need not mix the remaining air and/or particles—the separate flows from the four impactors could be maintained in separate flow paths for any other purpose, such as separate collections for the remaining particles.

Likewise it should be noted that air approaching inlet plate 1 could be directed there by a conduit or in an inlet chamber. This would be especially useful if the air sample was obtained as a positive air flow rather than a vacuum— that is, if a pump were located upstream of the sampler rather than downstream of it. It is expected, however, that more often the exhaust 20 will be connected to a vacuum pump— that is, to a pump for pulling air through the sampler in the direction of the exhaust.

The size of the inlet nozzle for each individual impactor is preferably selected according to desired 50% cut-off sizes, and outlet nozzles are sized to allocate the flow through each individual collector while observing equal pressure drops across the sampler and across each individual impactor so that:

$$\Delta P_S = \Delta P_{1In} + \Delta P_{1Out} = \Delta P_{2In} + \Delta P_{2Out} = P_{3In} + \Delta P_{3Out} \cdots = \Delta P_{NIn} + \Delta P_{NOut},$$

$\Delta P_S$ is the pressure drop across the whole sampler, and $\Delta P_{iIn}$ and $\Delta P_{iOut}$ are pressure drops across the inlet and outlet orifices for individual impactors. Once the size of the inlet nozzle for one of the impactors is selected according to the predetermined 50% cut-off and flow rate the size of the nozzle at the outlet is determined using the assumption that pressure drop across the nozzle is approximately equal to the dynamic pressure of the air jet:

$$\Delta P = \frac{1}{2}\rho V_0,$$

where $\rho$ is air density and $V_0$—average air velocity in the nozzle.

TABLE 1

Parameters of round-nozzle impactors to be incorporated in three-, four-, and five-impactor sampler designed to approximate a respirable convention at an overall sampling flow rate of 4.0 L/min. Each individual impactor has a single inlet nozzle.

| | Number of individual impactors, N | Flow rate through individual impactor, $Q_i$, L/min | Cut-off size, $d_{50}$, μm | Diameter of Inlet nozzle, $d_{In}$, mm | Air velocity in inlet nozzle, $V_O$ m/s | Reynolds number, Re | Diameter of outlet orifice, $d_{Out}$, mm |
|---|---|---|---|---|---|---|---|
| Sampler 1 | 3 | 1.3 | 2.4 | 1.95 | 7.44 | 967 | 3.62 |
| | | | 4.0 | 2.72 | 3.82 | 694 | 2.05 |
| | | | 6.2 | 3.62 | 2.16 | 521 | 1.95 |
| Sampler 2 | 4 | 1.0 | 2.2 | 1.68 | 7.52 | 842 | 3.44 |
| | | | 3.5 | 2.27 | 4.12 | 623 | 1.80 |
| | | | 4.6 | 2.72 | 2.87 | 520 | 1.72 |
| | | | 6.6 | 3.44 | 1.79 | 411 | 1.68 |
| Sampler 3 | 5 | 0.8 | 1.9 | 1.42 | 8.42 | 797 | 3.35 |
| | | | 3.2 | 1.98 | 4.33 | 572 | 1.52 |
| | | | 4.0 | 2.30 | 3.21 | 492 | 1.46 |
| | | | 5.0 | 2.66 | 2.40 | 425 | 1.44 |
| | | | 7.1 | 3.35 | 1.51 | 338 | 1.42 |

Table 1 includes impactor parameters estimated for samplers containing three, four and five round-nozzle impactors (each with a single inlet nozzle) with overall performances approximating respirable curves at a sampling flow rate of 4.0 Lpm.

TABLE 2

Parameters of rectangular-nozzle impactors to be incorporated in three-, four-, and five-impactor samplers designed to approximate a respirable convention at an overall sampling flow rate of 4.0 L/min. Nozzle length, the longer dimension of the rectangular opening for all impactors, is 8.0 mm. Each individual impactor has a single inlet nozzle.

| | Number of individual impactors, N | Flow rate through individual impactor, $Q_i$, L/min | Cut-off size, $d_{50}$, μm | Width of inlet nozzle, $W_{In}$, mm | Air velocity in inlet nozzle, $V_O$ m/s | Reynolds number, Re | Width of outlet orifice, $W_{Out}$, mm |
|---|---|---|---|---|---|---|---|
| Sampler 4 | 3 | 1.3 | 2.4 | 0.52 | 5.34 | 370 | 1.32 |
| | | | 4.0 | 0.86 | 3.23 | 370 | 0.59 |
| | | | 6.2 | 1.32 | 2.10 | 370 | 0.52 |
| Sampler 5 | 4 | 1.0 | 2.2 | 0.41 | 5.06 | 278 | 1.22 |
| | | | 3.5 | 0.65 | 3.21 | 278 | 0.49 |
| | | | 4.6 | 0.85 | 2.45 | 278 | 0.44 |
| | | | 6.6 | 1.22 | 1.71 | 278 | 0.41 |
| Sampler 6 | 5 | 0.8 | 1.9 | 0.32 | 5.21 | 222 | 1.18 |
| | | | 3.2 | 0.54 | 3.09 | 222 | 0.38 |
| | | | 4.0 | 0.67 | 2.49 | 222 | 0.35 |
| | | | 5.0 | 0.83 | 2.01 | 222 | 0.33 |
| | | | 7.1 | 1.18 | 1.41 | 222 | 0.32 |

Table 2 is for samplers similar to those of Table 1 but with rectangular-nozzle impactors. It is well known that performance of the impactor depends on nozzle size and flow rate through it, nozzle-to plate distance, nozzle throat length, and Reynolds number, Re, of the air jet: Rader, D. J., and Marple, V. A., "Effect of Ultra-Stokesian Drag and Particle Interception on Impaction Characteristics," *Aerosol Sci. Technolo.* 4:141–156 (1985); Marple, V. A., and Willeke, K., "Impactor Design," *Atmos. Envir.* 10:891–896 (1976). In addition, characteristics of the impactor are influenced by absence or presence of a tapered inlet: Jurcik, B and Wang, H. C. "On the Shape of Impactor Efficiency Curves" *Aerosol Sci. Technol.* 26:1139–1147, (1995), the size and surface characteristics of collection substrate employed: Huang, C. H., and Tsai, C. J. "Influence of Impactor Plate Diameter and Particle Density on the Collection Efficiency of Round-Nozzle Inertial Impactors" *Aerosol Sci. Technol.* 36:714–720, (2002); Huang, C. H., Tsai, C. J., and Shih, T. S. "Particle Collection Efficiency of an Inertial Impactor with Porous Metal Substrates" *J. Aerosol Sci.* 32:1035–1044 (2001). Taking into account the above and, also, our own experience while testing impactors of similar geometry [Trakumas S., Hall P. "Modification and Validation of Diesel Particulate Matter Cassette for PM-1.0 Sampling at Different Flow Rates, p. 19 in *Abstracts of American Industrial Hygiene Conference & Exposition*, San Diego, Calif. USA. (2002), $\sqrt{Stk_{50}}$ was set at 0.38 for round nozzle impactors and 0.62 for rectangular impactors in the estimates in Tables 1 and 2.

EXAMPLE 1

Figure 5:
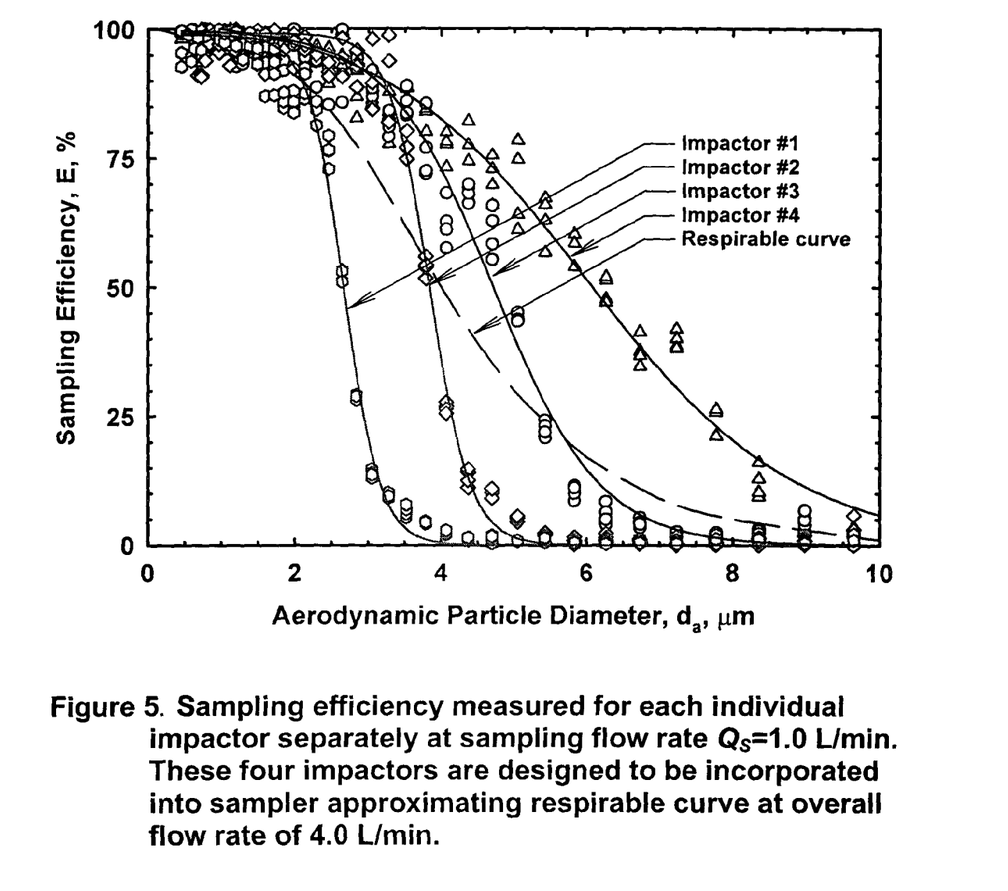
FIG. 5 shows the sampling efficiencies of the four parallel collectors described in Example 1.
Figure 6:
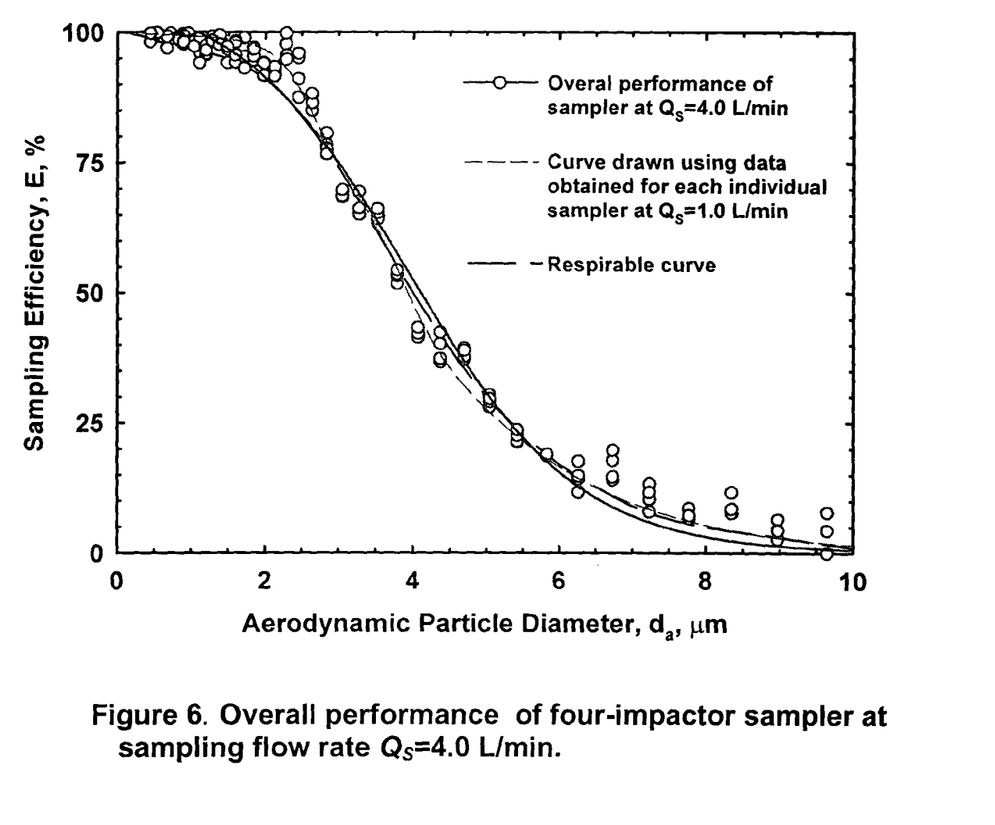
FIG. 6 shows the overall sampling efficiency of the sampler described in Example 1.

A sampler containing four parallel round-nozzle impactors and designed to approximate a respirable convention at 4.0 L/min (Table 1.) was machined and tested. The sampler incorporated a design similar to FIGS. 1–4 and the specifications of the 4-impactor design in Table 1 (Sampler 2). Experimental data are presented in FIGS. 5 and 6. Sampling efficiency was obtained by measuring particle concentration upstream and downstream of the sampler using an Aaerodynamic Particle Sizer (APS, Model 3320, TSI Inc., St. Paul, Minn.). FIG. 5 shows sampling efficiency of each separate impactor tested at 1.0 L/min (¼ of total flow). The dashed curve in FIG. 5 represents the respirable convention—the curve the sampler was designed to approximate. Table 1 shows that predicted $d_{50}$ for impactors 1–4 at $Q_S$=1.0 L/min is 2.2, 3.5, 4.6 and 6.6 μm. Experimentally obtained 50% cut-off sizes were 2.7, 3.8, 4.7, and 6.0 μm accordingly (FIG. 6). As can be seen the experimental data is in good agreement with theoretical prediction. FIG. 6 shows the sampling efficiency of the whole sampler at 4.0 L/min sampling flow rate: circles represent data obtained during four measurements and the solid line is a mathematical approximation through all experimental points; the thin dashed line is overall performance of the sampler estimated using experimental data obtained for each of four impactors individually as shown in FIG. 5; the thicker dashed line represents the respirable curve.

Good agreement between the curve representing the respirable convention and data obtained experimentally (FIG. 6) indicates that the respirable curve can be approximated with high accuracy using a sampler containing a plurality of impactors in parallel. The methods and data discussed herein may be used to design a multiimpactor sampler with characteristics approximating any predetermined curve at a selected flow rate.

The numbers presented in Tables 1 and 2, and the data displayed in FIGS. 5 and 6, all represent configurations in which, for each parallel impactor (collector), there is a single inlet nozzle and a single outlet orifice. Persons skilled in the art will recognize that it is possible to have more than one inlet nozzle and/or more than one exit orifice in one or more collectors. Using more than one inlet nozzle or outlet orifice, or both, in a single impactor can permit better control over air velocities, Reynolds numbers, and pressure drops to suit a specific operation. This can be especially useful when designing a sampler for high sampling flow rates.

Table 3 illustrates some types of variations of the invention that are possible at a flow rate ten times that of Tables 1 and 2. Three samplers are described, each having four impactors but the number of nozzles per impactor is different in each sampler. Each suggested impactor proposed in Table 3 receives one-fourth of the 40 liters per minute air flow of the sampler. Note that the cut-off sizes of the four nozzles in each impactor is identical for all three samplers while all the other specifications are different; the pressure drop for each sampler is maintained for all the impactors included in it. Our invention is not limited to use in portable or personal air samplers, but can be used in stationary room or outdoor air samplers or in any location where significantly higher flow rates may be useful. There is no theoretical upper limit to the sampler flow rate as a basis for designing a sampler.

TABLE 3

Examples of three samplers, each containing four parallel impactors with different numbers of inlet nozzles and a single outlet orifice. All samplers are designed to approximate a respirable convention at an overall sampling flow rate of 40.0 L/min. Flow rate through each individual impactor is 10.0 L/min.

|  | Number of inlet nozzles in an individual impactor, n | Cut-off size, $d_{50}$, μm | Diameter of inlet nozzle, $d_{In}$, mm | Air velocity in inlet nozzle, $V_O$ m/s | Reynolds number, Re | Diameter of outlet orifice, $d_{Out}$, mm | Pressure drop across sampler, ΔP, in H$_2$O |
|---|---|---|---|---|---|---|---|
| Sampler 7 | 1 | 2.2 | 3.60 | 16.37 | 3930 | 7.40 | 0.685 |
|  | 1 | 3.5 | 4.90 | 8.84 | 2887 | 3.85 |  |
|  | 1 | 4.6 | 5.80 | 6.31 | 2439 | 3.69 |  |
|  | 1 | 6.6 | 7.40 | 3.88 | 1912 | 3.60 |  |
| Sampler 8 | 5 | 2.2 | 2.10 | 9.62 | 1347 | 9.62 | 0.237 |
|  | 5 | 3.5 | 2.85 | 5.23 | 993 | 5.03 |  |
|  | 5 | 4.6 | 3.40 | 3.67 | 832 | 4.81 |  |
|  | 5 | 6.6 | 4.30 | 2.30 | 658 | 4.70 |  |
| Sampler 9 | 10 | 2.2 | 1.68 | 7.52 | 842 | 10.75 | 0.145 |
|  | 10 | 3.5 | 2.25 | 4.19 | 629 | 5.71 |  |
|  | 10 | 4.6 | 2.70 | 2.91 | 524 | 5.44 |  |
|  | 10 | 6.6 | 3.40 | 1.84 | 416 | 5.31 |  |

A further example of the versatility of our technique for designing samplers is shown in Table 4, where the specifications are given for a yet another sampler having four impactors. Two of the impactors have two inlet nozzles, two have five inlet nozzles, and each impactor has a single outlet. The sampler Is designed for an overall flow rate of four Liters per minute. The air flow is evenly split by the architecture of the impactors themselves, into four equal flow paths or streams of one Liter per minute. The diameters of the plural inlet nozzles are calculated according to the above-explained relationships to provide the desired cut-off sizes shown in Table 4.

TABLE 4

Example of a parallel impactor sampler containing four impactors with different numbers of inlet nozzles and a single outlet orifice. The sampler is designed to approximate a respirable convention at an overall sampling flow rate of 4.0 L/min and 1.0 L/min flow through each individual impactor. Note: the sampler employs only two inlet nozzle sizes, but achieves four different cut-off sizes.

| Number of inlet nozzles in an individual impactor, n | Cut-off size, $d_{50}$, μm | Diameter of Inlet nozzle, $d_{In}$, mm | Air velocity in inlet nozzle, $V_O$ m/s | Reynolds number, Re | Diameter of outlet orifice, $d_{Out}$, mm | Pressure drop across sampler, $\Delta P$, in $H_2O$ |
|---|---|---|---|---|---|---|
| 2 | 2.2 | 1.32 | 16.37 | 536 | 4.30 | 0.093 |
| 5 | 3.5 | 1.32 | 8.84 | 214 | 1.93 | |
| 2 | 4.6 | 2.15 | 6.31 | 329 | 1.92 | |
| 5 | 6.6 | 2.15 | 3.88 | 165 | 1.87 | |

Persons skilled in the art will also recognize that the flow rates are equal in the parallel paths described in Tables 1, 2, 3, and 4, but they need not be designed to have equal flow rates although the collectors will continue to have equal pressure drops across them. For example, if there is a need or desire to collect a significantly different amount or portion of one size particle compared to another, the air flow split may be calculated to provide larger or smaller portions of the sampler air to one or more cut-off sizes than is fed to the other collectors.

It should be understood that, although we have designed our preferred samplers with the objective of collecting small respirable particles on a filter or other common collector, our design is as well conceived for the ability to analyze or count particles collected in the individual impactors or collectors; it is not essential to collect particles passing through the exit orifices, nor is it necessary to collect them in a single or common repository—separate repositories may be maintained for particles passing through the separate impactors. For example, a filter may be divided into four segments to receive perhaps somewhat different types or ranges of particles. If some other type of final collector is used (other than a filter or identical areas of a filter) the designs should take into account the effects noted above on flow rates, pressure drops and other effects and variables throughout the system. Also, it is not necessary for all the impactors to have identical impactor surfaces. As is known in the art, impactor surfaces may be made of oil, water, various adhesive coatings, synthetic polymers, wax, agar, or any other sticky substance or attractive material.

It may also be observed by persons skilled in the art that, while our sampler will be designed for a particular overall flow rate, such as the four and forty liters per minute used in the above presentations, the effects of a change in overall flow rate are mathematically predictable. It is therefore contemplated that, if under some circumstances one may want to deliberately deviate from the design flow rate of a sampler, the effects of doing so can be computed and the appropriate expectable curves can be generated by computer or otherwise.

Figure 7:
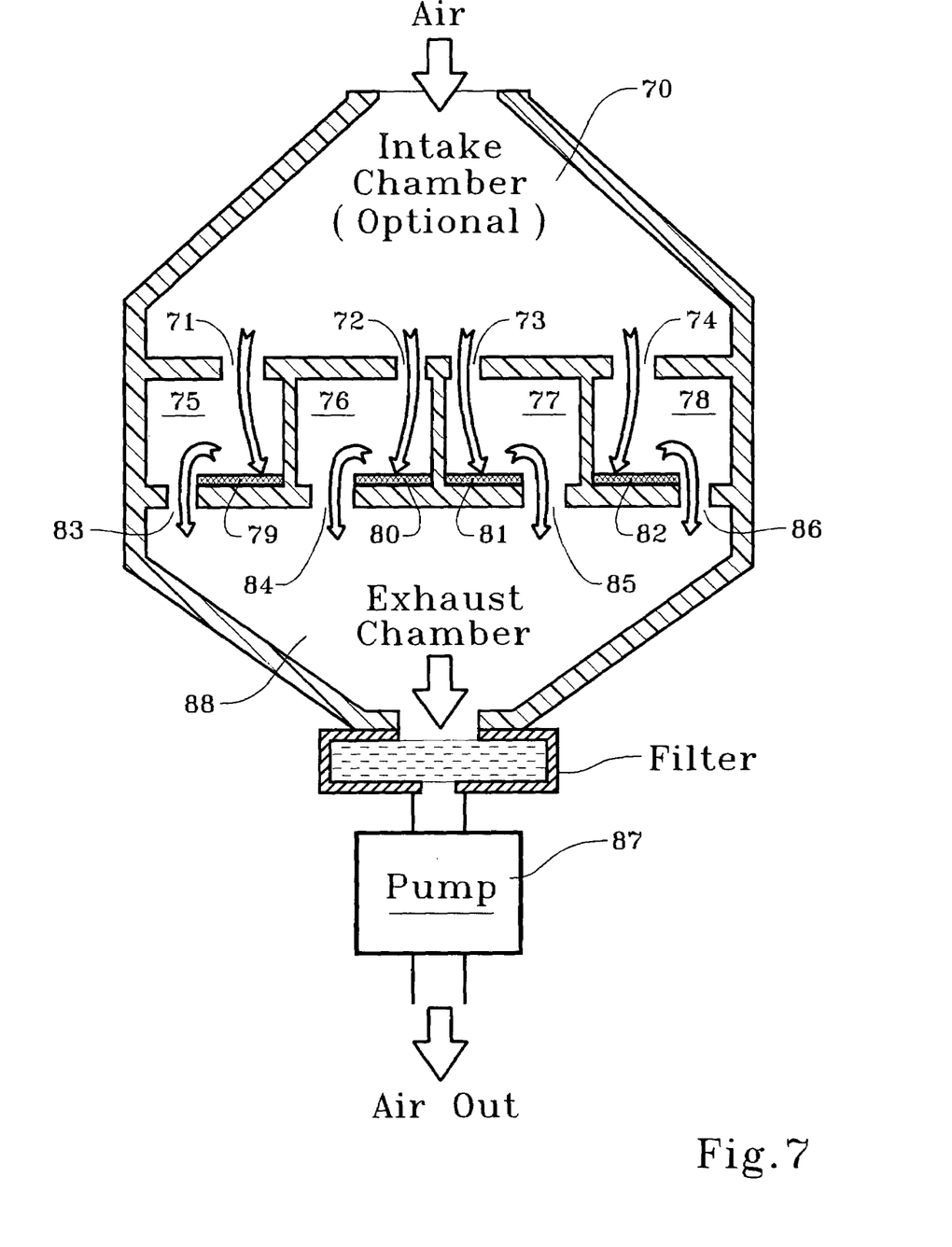
FIG. 7 is a simplified flow diagram.

In FIG. 7, a simplified flow chart illustrates the multiple air flow paths utilized in our invention. Air enters the four impactors (collectors) from the environment through an optional intake chamber 70. It passes through nozzles 71, 72, 73, and 74, which may have different opening areas. The parallel impactors 75, 76, 77, and 78 have separate air flows as illustrated; they also have collection surfaces 79, 80, 81 and 82 and outlet orifices 83, 84, 85, and 86. Air is drawn by pump 87 through all the impactors at a predetermined overall flow rate. Air passing through outlet orifices 83, 84, 85, and 86 is mixed in exhaust chamber 88 and passed through filter 89 to the pump 87 and then finally to the atmosphere. As explained elsewhere herein, the intake chamber 70 is optional. The filter may be replaced by other collection devices, and indeed may be divided for collecting from each separate flow path if desired, but the pump is intended to continue to draw air at a predetermined overall flow rate through the sampler, and to that end the entire air flow should be mixed by the time it passes through the pump 87. As indicated elsewhere herein, our invention is not limited to the four parallel impactors or collectors illustrated in this FIG. 7, but may utilize any plural number of such devices. It should also be understood that the numbers and sizes of the nozzles and outlet orifices may be varied as discussed elsewhere herein.

Therefore, it is seen that our invention in one aspect comprises an air sampler for collecting particles from a stream of air, the air sampler comprising (a) an inlet plate for the stream of air, the inlet plate including at least two inlet nozzles (b) a collection chamber downstream of each of the at least two inlet nozzles, each of the collection chambers including a collector surface and at least one outlet orifice, whereby, at a predetermined air flow rate for the air sampler, the pressure drop across each of the collection chambers is substantially equal to the overall pressure drop of the air sampler.

In another aspect, our invention comprises a plurality of parallel impactors, each of the impactors having at least one inlet nozzle and at least one outlet orifice wherein either or both (a) at least one of the inlet nozzles is of a size different from the other inlet nozzles or (b) at least one of the outlet orifices is of a size different from the other outlet orifices, whereby the parallel impactors will permit the passage of air therethrough at predetermined flow rates when the air sampler is operated at a predetermined overall flow rate for the air sampler.

Again, our invention includes a method of sampling air-borne particles comprising substantially continuously passing an air sample at a substantially constant selected sampler flow rate through a plurality of parallel collectors, each of the collectors having a selected collector flow rate.

Our invention also includes a method of designing an air sampler for collecting particles in air comprising (a) selecting desired cut-off sizes for at least two different desired particle selections from the air, (b) selecting a desired overall air flow rate for the introduction of air to the air sampler, (c)

calculating inlet nozzle dimensions for each of the cut-off sizes and designing inlet nozzles therefor to be placed in an inlet plate, the inlet nozzles leading to segregated collection chambers, and (d) calculating dimensions of outlet orifices in the collection chambers to achieve one of the cut-off sizes for each of the collection chamber.

The invention claimed is:

1. An air sampler comprising a plurality of parallel impactors, each of said impactors having at least one inlet nozzle and at least one outlet orifice wherein either or both (a) at least one of said inlet nozzles is of a size different from the other inlet nozzles or (b) at least one of said outlet orifices is of a size different from said other outlet orifices, whereby said parallel impactors will permit the passage of air therethrough at predetermined flow rates when said air sampler is operated at a predetermined overall flow rate for said air sampler.

2. Air sampler of claim 1 wherein said impactors have inlet nozzles and outlet orifices designed to achieve said predetermined impactor flow rates at said predetermined sampler flow rate.

3. Air sampler of claim 1 wherein said nozzles and said orifices are sized so that said predetermined flow rates in said parallel impactors are substantially equal when said air sampler is operated at a predetermined overall flow rate for said air sampler.

4. Air sampler of claim 1 wherein said inlet nozzles and said outlet orifices are chosen to approximate at least one sampling curve selected from published sampling curve standards.

5. Air sampler of claim 1 including at least one collector for collecting particles which pass through at least one impactor.

6. Air sampler of claim 5 wherein said collector comprises a filter.

7. Air sampler of claim 1 including an air intake chamber for directing air to said nozzles.

* * * * *

UNITED STATES PATENT AND TRADEMARK OFFICE
CERTIFICATE OF CORRECTION

PATENT NO. : 7,073,402 B2
APPLICATION NO. : 10/639564
DATED : July 11, 2006
INVENTOR(S) : Saulius Trakumas It is certified that error appears in the above-identified patent and that said Letters Patent is hereby corrected as shown below:

Item 56 References Cited, Other Publications, Page 2, line 10 cancel "Impactor Efficiency. Curves" and insert --Impactor Efficiency Curves--

Column 1, Line 49 cancel "Cincinnati Ohio" and insert --Cincinnati OH--

Column 3, Line 19, insert --or--

Column 3, Line 24 delete "or"

Column 6, Line 48 cancel "$\Delta P_s = \Delta P_{1In} + \Delta P_{1Out} = \Delta P_{2In} + \Delta P_{2Out} = \Delta P_{3In} + \Delta P_{3Out} \ldots = \Delta P_{NIn} + \Delta P_{NOut}$". and insert --$\Delta P_s = \Delta P_{1In} + \Delta P_{1Out} = \Delta P_{2In} + \Delta P_{2Out} = \Delta P_{3In} + \Delta P_{3Out} \ldots = \Delta P_{NIn} + \Delta P_{NOut}$--

Signed and Sealed this

Twenty-first Day of August, 2007

JON W. DUDAS
*Director of the United States Patent and Trademark Office*